United States Patent [19]

Hug

[11] Patent Number: 4,472,574
[45] Date of Patent: Sep. 18, 1984

[54] PROCESS FOR THE MANUFACTURE OF A CEPHEM CARBOXYLIC ACID DERIVATIVE

[75] Inventor: Rudolf Hug, Riehen, Switzerland

[73] Assignee: Hoffmann-LaRoche Inc., Nutley, N.J.

[21] Appl. No.: 293,224

[22] PCT Filed: Jul. 3, 1981

[86] PCT No.: PCT/CH81/00073
§ 371 Date: Aug. 10, 1981
§ 102(e) Date: Aug. 10, 1981

[30] Foreign Application Priority Data

May 22, 1981 [CH]  Switzerland .................. 3362/81

[51] Int. Cl.³ .................................. C07D 501/04
[52] U.S. Cl. ............................................ 544/26
[58] Field of Search ................................ 544/26

[56] References Cited
U.S. PATENT DOCUMENTS 4,178,443  5/1978  Montavon et al. .......... 544/27
4,317,907  3/1982  Saikawa et al. ............ 544/26
4,327,210  4/1982  Montavon et al. .......... 544/26

FOREIGN PATENT DOCUMENTS 5  6/1978  European Pat. Off. .
2804896  8/1978  Fed. Rep. of Germany .
1565941  4/1980  United Kingdom .

Primary Examiner—Paul M. Coughlan, Jr.
Attorney, Agent, or Firm—Jon S. Saxe; Bernard S. Leon; George W. Johnston

[57] ABSTRACT

A process is disclosed for the manufacture of (7R,8R)-7-amino-3-[[(2,5-dihydro-6-hydroxy-2-methyl-5-oxo-as-triazin-3-yl)-thio]-methyl]-3-cephem-4-carboxylic acid by reacting (7R, 8R)-7-amino-cephalosporanic acid with 2,5-dihydro-6-hydroxy-3-mercapto-2-methyl-5-oxo-as-triazine in the presence of boron trifluoride or a complex compound thereof in a polar organic solvent and is characterized by precipitating the reaction product which is in aqueous phase in the form of the free acid by adding a base up to a pH-value of about 1.4–2.0, whereupon the desired pure acid can be separated.

9 Claims, No Drawings

PROCESS FOR THE MANUFACTURE OF A CEPHEM CARBOXYLIC ACID DERIVATIVE

The (7R,8R)-7-amino-3-[[(2,5-dihydro-6-hydroxy-2-methyl-5-oxo-as-triazin-3-yl)-thio]-methyl]-3-cephem-4-carboxylic acid is a valuable intermediate product for the manufacture of antibacterially-active cephalosporin derivatives, for example the (7R,8R)-7-[2-(2-amino-4-thiazolyl)-2-(Z-methoxyimino)-acetamido]-3-[[2,5-dihydro-6-hydroxy-2-methyl-5-oxo-as-triazin-3-yl)-thio]-methyl]-3-cephem-4-carboxylic acid. These derivatives can be obtained in a known manner from the named intermediate product by acylating the 7-amino group with corresponding carboxylic acids or reactive carboxylic acid derivatives.

It is known, for example from German Offenlegungsschrift 2 804 896, that compounds of the type of intermediate product named at the beginning, namely (7R,8R)-7-amino-3-thiomethyl-3-cephem-4-carboxylic acids with substituted thio group, can be manufactured by reacting the (7R,8R)-7-amino-cephalosporanic acid with a thiol compound in the presence of boron trifluoride or a complex compound thereof in a polar organic solvent. The working-up from the reaction solution is effected in the case of this known method by rendering alkaline with aqueous base up to a pH of about 3.5–4.0, whereby the product precipitates in the form of the free carboxylic acid which is subsequently separated, washed and dried.

If the 2,5-dihydro-6-hydroxy-3-mercapto-2-methyl-5-oxo-as-triazine is employed as the thiol compound in this process, with the usual working-up with aqueous base at pH 3.5–4.0 the desired intermediate product, namely the (7R,8R)-7-amino-3-[[(2,5-dihydro-6-hydroxy-2-methyl-5-oxo-as-triazin-3-yl)-thio]-methyl]-3-cephem-4-carboxylic acid, is surprisingly obtained not entirely in the form of the free carboxylic acid, but as a mixture with the mono-salt (e.g. as a mixture with the monoammonium salt). This mixture is associated with certain disadvantages, in that it results with a considerable amount of unidentified impurities (>10%). Further, mono-salts of the carboxylic acid are as a rule not suited or only ill-suited for the subsequent 7-acylation, since the 7-acylation should preferably be carried out in anhydrous solution, i.e. in solution in an organic solvent, namely because of the advantages associated therewith having regard to the stability of the reaction participants as well as the yields and purity of the reaction product. The free carboxylic acid required for the 7-acylation is, indeed, not itself soluble in the organic solvent, but it is readily brought into solution by silylation or reaction with a trialkylamine. The mono-salts (insofar as they are not trialkylammonium salts) are, however, neither soluble in organic solvents nor are they brought into solution in the stated manner; they are accordingly, as already stated, unsuitable starting materials for the 7-acylation.

It has now been found that the (7R,8R)-7-amino-3-[[(2,5-dihydro-6-hydroxy-2-methyl-5-oxo-as-triazin-3-yl)-thio]-methyl]-3-cephem-4-carboxylic acid is obtained entirely as the desired, free carboxylic acid when the pH-value is adjusted to about 1.4–2.0, especially to 1.6–1.8. It is thereby surprising that at this pH-value the 7-amino group is not present as the acid addition salt, in which form it would be blocked for subsequent acylation reactions and thus would not be usable.

By the precipitation of the (7R,8R)-7-amino-3-[[(2,5-dihydro-6-hydroxy-2-methyl-5-oxo-as-triazin-3-yl)-thio]-methyl]-3-cephem-4-carboxylic acid as the free carboxylic acid at a pH-value of about 1.4–2.0 there is now obtained after separation, e.g. by filtration, as well as washing with usual solvents and drying, a particularly pure product, namely a product which is as a rule about 98–100% pure (corresponding purity of the mixture of carboxylic acid/sodium salt precipitated at pH 3.5–4.0 is <90%), which in contrast to the ammonium salt can be transformed in non-aqueous, organic phase with silylating agents, e.g. with N,O-bis-(trimethylsilyl)-acetamide, trimethylsilylacetamide, trimethylchlorosilane or dimethyldichlorosilane, or with a trialkylamine, e.g. triethylamine, into the corresponding, soluble product. The latter can subsequently be converted in the organic phase directly with the acylating agent in high yield and purity into corresponding, antibacterially-active cephalosporin derivatives.

The process in accordance with the invention is accordingly concerned with the manufacture of (7R,8R)-7-amino-3-[[(2,5-dihydro-6-hydroxy-2-methyl-5-oxo-as-triazin-3-yl)-thio]-methyl]-3-cephem-4-carboxylic acid by reacting (7R,8R)-7-amino-cephalosporanic acid with 2,5-dihydro-6-hydroxy-3-mercapto-2-methyl-5-oxo-as-triazine in the presence of boron trifluoride or a complex compound thereof in a polar organic solvent and is characterised by precipitating the reaction product in aqueous phase in the form of the free acid by adding a base up to a pH-value of about 1.4–2.0, whereupon the pure acid can be separated.

The reaction of the above reaction participants is effected in a known manner in the presence of boron trifluoride or a complex compound thereof, e.g. in the presence of the complex with diethyl ether, acetic acid, acetonitrile etc. As a rule, the boron triluoride or one of its complex compounds is used in molar excess, e.g. 2 to 7 mol per mol of (7R,8R)-7-amino-cephalosporanic acid. The reaction is effected in anhydrous medium, namely in a polar organic solvent, preferably in acetonitrile or glacial acetic acid, and the reaction temperature lies, although not critically, preferably between room temperature and about 50° C.

After completion of the reaction, the reaction mixture is preferably diluted firstly with water to a water content of about 15–30 vol.-%. Subsequently, the pH-value is adjusted to a pH-value of about 1.4–2.0, preferably 1.6–1.8, with the aid of a suitable base, e.g. with sodium or potassium hydroxide, with a sterically hindered amine, such as triethylamine or diisopropylethylamine, but preferably with ammonia, whereby the reaction product precipitates. The water content should preferably remain within the limits of about 15–30 vol.-% during the precipitation. These limits can be maintained e.g. by adding the required water in the main before the base, which can then be added subsequently in anhydrous or concentrated aqueous form. Also, firstly only a small amount of water can be added or no water whatsoever and subsequently correspondingly diluted aqueous base can be used. As a practical compromise it is convenient firstly to add only a part of the water (e.g. about 15–25 vol. %) and then to adjust the mixture with correspondingly diluted aqueous base up to a water content of about 20–30 vol. % and a pH-value of about 1.4–2.0.

Although the invention is not limited to the use of a water content range of about 15–30 vol.-%, this represents an advantageous embodiment of the process in accordance with the invention. With lower water content the process is less advantageous, since then the boric acid formed in the reaction as a byproduct begins to precipitate, whereby the product is contaminated. With higher water content there is obtained a difficultly filterable product which partially decomposes upon drying.

Within the preferred limits of about 15–30 vol.-% of water the precipitated precipitate can be readily separated in pure form, e.g. by filtration, washed with suitable solvents, e.g. with water, acetonitrile/water and/or acetone, and dried with minimum decomposition loss. There is thus obtained the (7R,8R)-7-amino-[[(2,5-dihydro-6-hydroxy-2-methyl-5-oxo-as-triazin-3-yl)-thio]-methyl]-3-cephem-4-carboxylic acid in particularly pure (normally 98–100%) and stable form.

The following Examples illustrate the invention without limiting it.

EXAMPLE 1

30 g of (7R,8R)-7-amino-cephalosporanic acid and 17.5 g of 2,5-dihydro-6-hydroxy-3-mercapto-2-methyl-5-oxo-as-triazine are suspended in 425 ml of acetonitrile and warmed to 50° C. under nitrogen gasification. As soon as this temperature is attained, 73 g of boron trifluoride etherate are added. After 30 minutes, [the mixture] is cooled to 10° C. and 116 ml of water are added. Subsequently, the pH-value is adjusted to 1.7 with about 70 ml of aqueous 12% ammonia, whereby the product precipitates. After stirring for 15 minutes, the product is filtered off under suction, washed in each case twice with 80% acetonitrile/water and acetone and dried. There are obtained 33.0 g (80.6%) of (7R,8R)-7-amino-3-[[(2,5-dihydro-6-hydroxy-2-methyl-5-oxo-as-triazin-3-yl)-thio]-methyl]-3-cephem-4-carboxylic acid of melting point 195°–198° C. (dec.). Content 98.0% in accordance with high-pressure liquid chromatographical analysis.

EXAMPLE 2

30 g of (7R,8R)-7-amino-cephalosporanic acid and 17.5 g of 2,5-dihydro-6-hydroxy-3-mercapto-2-methyl-5-oxo-as-triazine are suspended in 235 ml of acetonitrile and warmed to 35° C. under nitrogen gasification. As soon as this temperature is attained, a solution of 26.1 g of boron trifluoride in 105 ml of acetonitrile is added. After 30 minutes, [the mixture] is cooled to 10° C. and 128 ml of water are added. Subsequently, the pH-value is adjusted to 1.65 with about 42 ml of aqueous 12% ammonia, whereby the product precipitates. After stirring for 15 minutes, the product is filtered off under suction, washed in each case twice with 80% acetonitrile/water and acetone and dried. There are obtained 33.5 g (81.7%) of (7R,8R)-7-amino-3-[[(2,5-dihydro-6-hydroxy-2-methyl-5-oxo-as-triazin-3-yl)-thio]-methyl]-3-cephem-4-carboxylic acid of melting point 201°–203° C. (dec.). Content 99.5% in accordance with high-pressure liquid chromatographical analysis.

I claim:

1. A process for the manufacture of (7R,8R)-7-amino-3-[[(2,5-dihydro-6-hydroxy-2-methyl-5-oxo-as-triazin-3-yl)-thio]-methyl]-3-cephem-4-carboxylic acid comprising:

(a) reacting (7R,8R)-7-amino-cephalosporanic acid with 2,5-dihydro-6-hydroxy-3-mercapto-2-methyl-5-oxo-as-triazine in the presence of boron trifluoride or a complex compound thereof in a polar organic solvent so as to form a reaction mixture; and (b) adding a base thereto to increase the pH-value of the reaction mixture to about 1.4 to about 2.0 and thereby precipitate (7R,8R)-7-amino-3-[[(2,5-dihydro-6-hydroxy-2-methyl-5-oxo-as-triazin-3-yl)-thio]-methyl]-3-cephem-4-carboxylic acid.

2. The process of claim 1 wherein ammonia is used as the base.

3. The process of claim 1 wherein the base is added to adjust the pH-value of the reaction mixture to between about 1.6 and about 1.8.

4. The process of claim 1 further comprising maintaining a water content of the reaction mixture of about 15 to about 30 vol.-% while adding the base.

5. The process of claim 1 further comprising:

(a) prior to the step of adding the base, adding water to the reaction mixture to a water content of about 15 to about 25 vol.-%.

(b) prior to the step of adding the base, adding water to the base to a water content of about 15 to about 25 vol.-%; and (c) maintaining a water content of the reaction mixture of about 15 to about 30 vol.-% while adding the diluted base.

6. A process for producing (7R,8R)-7-amino-3[[(2,5-dihydro-6-hydroxy-2-methyl-5-oxo-as-triazin-3-yl)-thio]-methyl]-3-cephem-4-carboxylic acid comprising:

(a) reacting (7R,8R)-7-amino-cephalosporanic acid with 2,5-dihydro-6-hydroxy-3-mercapto-2-methyl-5-oxo-as-triazine in the presence of boron trifluoride or a complex compound thereof in a polar organic solvent thereby to produce a reaction mixture; and (b) diluting the reaction mixture with water to a water content of about 15 to about 25 vol.-%; and (c) adjusting the pH of the reaction mixture to between about 1.4 and about 2.0 with a base thereby to produce (7R,8R)-7-amino-3-[[(2,5-dihydro-6-hydroxy-2-methyl-5-oxo-as-triazin-3-yl)-thio]-methyl]-3-cephem-4-carboxylic acid.

7. The process of claim 6 wherein the pH is adjusted to about 1.6 to about 1–8.

8. The process of claim 7 wherein the base is ammonia.

9. A process for producing (7R,8R)-7-amino-3[[(2,5-dihydro-6-hydroxy-2-methyl-5-oxo-as-triasin-3-yl)-thio]-methyl]-3-cephem-4-carboxylic acid comprising:

(a) reacting (7R,8R)-7-amino-cephalosporanic acid with 2,5-dihydro-6-hydroxy-3-mercapto-2-methyl-5-oxo-as-triazine in the presence of boron trifluoride or a complex compound thereof so as to produce a reaction product in the aqueous phase; and (b) precipitating the reaction product in the aqueous phase by adding thereto a base to obtain a pH-value of about 1.4 to about 2.0 so as to precipitate (7R,8R)-7-amino-3[[(2, 5-dihydro-6-hydroxy-2-methyl-5-oxo-as-triazin-3-yl)-thio]-methyl]-3-cephem-4-carboxylic acid.

* * * * *